United States Patent [19]

Gruber et al.

[11] 4,370,490
[45] Jan. 25, 1983

[54] PROCESS FOR PRODUCING METHACRYLIC ACID BY OXIDATIVE DEHYDRATION OF ISOBUTYRIC ACID AND CATALYST THEREFOR

[75] Inventors: Wilhelm Gruber, Darmstadt; Günter Schröder, Ober-Ramstadt, both of Fed. Rep. of Germany

[73] Assignee: ROHM GmbH Chemische Fabrik, Darmstadt, Fed. Rep. of Germany

[21] Appl. No.: 297,279

[22] Filed: Aug. 28, 1981

[30] Foreign Application Priority Data

Aug. 28, 1980 [DE] Fed. Rep. of Germany ....... 3032423
Feb. 2, 1981 [DE] Fed. Rep. of Germany ....... 3103410

[51] Int. Cl.$^3$ .................. C07C 51/377; C07C 57/05; C07C 67/317
[52] U.S. Cl. ..................... 560/214; 562/599; 252/435; 252/437
[58] Field of Search .................. 560/214; 562/599

[56] References Cited

U.S. PATENT DOCUMENTS 4,061,673 12/1977 Onoda et al. ............... 562/599
4,249,020 2/1981 McNeil et al. .............. 560/214
4,307,247 12/1981 Shaw et al. ................ 560/214

FOREIGN PATENT DOCUMENTS 2118904 11/1972 Fed. Rep. of Germany .
2450878  4/1975 Fed. Rep. of Germany .
2517148 10/1975 Fed. Rep. of Germany .
2550979  5/1977 Fed. Rep. of Germany .
2722375 12/1977 Fed. Rep. of Germany .
50-4014   1/1975 Japan .
50-4017   2/1975 Japan .

Primary Examiner—Natalie Trousof
Assistant Examiner—L. Hendriksen
Attorney, Agent, or Firm—Oblon, Fisher, Spivak, McClelland & Maier

[57] ABSTRACT

Isobutyric acid is oxidatively dehydrogenated to methacrylic acid by passing a gaseous mixture of isobutyric acid, oxygen, nitrogen and optionally water vapor at temperatures of 300°–450° C. and pressures of 0.5 to 5 bar over a catalyst comprising molybdenum oxide, which also contains vanadium, phosphorous and a metal selected from the group consisting of alkali metals, alkaline earth metals, zinc, silver, aluminum, titanium, lead, manganese, iron, cobalt, nickel and tin, preferably precipitated on a solid silica support and calcined at 200° to 400° C. At conversion levels of 80 to 100% of the isobutyric acid used, a methacrylic acid selectivity of 60 to 74% is attained.

21 Claims, No Drawings

PROCESS FOR PRODUCING METHACRYLIC ACID BY OXIDATIVE DEHYDRATION OF ISOBUTYRIC ACID AND CATALYST THEREFOR

BACKGROUND OF THE INVENTION

1. Field of the Invention

This invention relates to production of methacrylic acid by oxidative dehydrogenation of isobutyric acid using contact catalysts, and more particularly to oxidative dehydrogenation of isobutyric acid using catalysts containing oxides of molybdenum, vanadium, and phosphorus. The invention also relates to catalysts useful in the oxidative dehydrogenation of isobutyric acid.

2. Description of the Prior Art

The synthesis of methacrylic acid and esters thereof which are important raw materials for the production of synthetic polymers is of great and growing economic importance. The dominant industrial method of preparing these monomers at present uses acetone as the starting material and proceeds via acetone cyanohydrin which is hydrolyzed to produce the most important monomer in the methacrylate series, methyl methacrylate. Other synthetic methods which start with isobutyraldehyde or olefins such as isobutylene, ethylene, or propylene have also attracted industrial interest.

German Offenlegungsschrift No. 25 17 148 discloses a process for producing methacrylic acid from methacrolein (derived from isobutylene or isobutyraldehyde) by gas phase catalytic oxidation with oxygen. The catalyst used in this oxidation has the formula:

$$Mo_{12}P_aX_bY_cW_dO_e,$$

wherein X represents vanadium, niobium and/or tantalum and Y represents cesium, potassium and/or thallium; a and b have values from 0.1 to 10, c has values from 0.1 to 8 and d has values from 0 to 10; the value of e depends on the valence of of the remaining atoms; and the sum of a+b+c has a value of 0.3 to 20.

A number of catalysts have been suggested for oxidative dehydrogenation of isobutyric acid to methacrylic acid.

Japanese Published Unexamined patent application, Publication No. 7,504,017 discloses a catalyst containing molybdenum, phosphorus, thallium, and oxygen as useful for the gas-phase dehydrogenation of isobutyric acid.

Japanese Published Unexamined patent application, Publication No. 7,504,014 discloses the use of molybdophosphoric acids or molybdovanadophosphoric acids treated with nickel sulfate, cobalt sulfate, or an alkali metal sulfate, as catalysts for the gas-phase oxidative dehydrogenation of isobutyric acid.

The oxidative dehydrogenation of alkanecarboxylic acids and their esters to $\alpha,\beta$-unsaturated aliphatic acids and esters using calcined iron/lead phosphate as the dehydrogenation catalyst has also been disclosed (German Offenlegungsschrift No. 24 50 878). Dehydrogenation of this class of compounds with oxygen using calcined precipitated phosphate containing bismuth, iron, and optionally lead is taught in German Offenlegungsschrift No. 21 18 904.

These prior art methods, however, are not entirely satisfactory. From the modern point of view, decisive importance is ascribed not only to capital expenditures, but also to considerations of the balance of energy and raw material costs in relation to the volume-time yield and the selectivity of the processes.

Thus, processes using contact catalysts based on iron phophate produce relatively low yields of isobutyric acid. Consequently, the unconverted isobutyric acid has to be recycled back into the process. Because of the very similar physical properties of isobutyric acid and methacrylic acid, separation of the two compounds on an industrial scale is uncertain and, in any case, expensive.

German Offenlegungsschrift No. 25 50 979 discloses the use of solid catalysts consisting essentially of molybdenum and/or tungsten or their respective oxides at temperatures between 300° and 500° C.

German Offenlegungsschrift No. 27 22 375 discloses a hydrothermal method of preparing catalysts based on heteropolyacids of an oxide or oxyacid of molybdenum, vanadium, phosphorus, and optionally tungsten which are suitable for oxidative dehydrogenation of isobutyric acid or its methyl ester and of methacrolein.

Studies of heterpolyacid catalysts have shown, however, that relatively high yields with good selectivity can be achieved only above 330° C. and in a relatively narrow temperature range (about 330° to 350° C.). Below this temperature range the yields fall off abruptly, while above 350° C. the catalyst is evidently irreversibly damaged so that the yield and the selectivity fall off markedly. Maintaining such a narrow temperature range at a relatively high temperature under the conditions of heterogeneous catalysis is difficult to realize in industrial practice if costs are to remain resonable. Accordingly, in practice, such catalysts have a limited life under the reaction conditions specified above.

Hence a need has continued to exist for a method of producing methacrylic acid by the catalytic oxidative dehydrogenation of isobutyric acid which has a good yield, high selectivity, and which uses a practical catalyst system.

SUMMARY OF THE INVENTION

Accordingly, it is an object of this invention to provide a process for producing methacrylic acid by the catalytic oxidative dehydrogenation of isobutyric acid.

A further object is to provide a process for producing methacrylic acid from isobutyric acid which has a good yield and high selectivity.

A further object is to provide an improved catalyst for the catalytic oxidative dehydrogenation of isobutyric acid to produce methacrylic acid.

These and other objects of the invention, as will become apparent from the specification which follows, have been achieved by a process for producing methacrylic acid by oxidative dehydrogenation of isobutyric acid with excellent yield and high selectivity comprising contacting isobutyric acid in the gas phase with a metal oxide catalyst which is substantially free of sulfate and comprises molybdenum oxide which may also contain vanadium, phosphorus, and a cation of a metal selected from the group consisting of alkali metals, alkaline earth metals, zinc, silver, aluminum, titanium, lead, maganese, iron, cobalt, nickel, and tin.

In general, the compounds which are particularly suited as catalysts for use in the process of this invention can be represented by the formula:

$$M_aMo_bV_cP_dO_e$$

wherein M is a metal selected from the group consisting of K, Rb, Cs, Be, Mg, Ba, Zn, Ca, Ag, Al, Ti, Pb, Mn, Fe, Co, Ni, and Sn, a is a number from 0.4 to 2.5, b is a number about equal to 12, c is a number from 1 to 2, d is a number from 0.5 to 3, and e is a number chosen to satisfy the valences and amounts of the other elements present in the catalyst.

DETAILED DESCRIPTION OF THE PREFERRED EMBODIMENTS

A preferred group of metals M comprises magnesium, calcium, and aluminum.

Those catalysts are particularly preferred in which b has the numerical value of ca. $6 \times a$, d is approximately equal to a, and c has a value of ca. $0.75 \times a$. A system of the approximate composition $A_{1.5-2}Mo_{12}V_{1.5}P_2O_{45-46}$ would be an example, where A stands for an alkali metal of the group potassium, rubidium and cesium. A particularly preferred composition is $$Cs_{1.5-2}Mo_{12}V_{1.5}P_2O_{45.8}.$$

The catalyst of this invention can be produced by starting with a molybdenum compound, such as molybdenum oxide or molybdic acid $H_2MoO_4$ or a salt thereof, such as the ammonium salt; a compound of pentavalent phosphorus, such as phosphoric acid or polyphosphoric acid or their salts, or phosphorous pentoxide; a vandium salt, such as a nitrate, carbonate, sulfate or halide or the salt of an organic acid or the oxide of vanadium; and a salt or hydroxide of the metal M, for example a metal halide, carbonate, nitrate, sulfate or the salt of an organic acid. If one of the metals mentioned is added to the reaction mixture for preparing the catalyst in the form of its sulfate, care must be taken that the sulfate portion is substantially completely removed during the production of the catalyst. Preferably none of the ingredients is used in sulfate form.

The catalyst can be produced by adapting the known method for producing complex metal oxide catalysts. For example, the catalyst system can be produced by mixing the components, dissolved or suspended in a fluid reaction medium such as water, while taking care that the distribution is as homogenous as possible. In particular when using ammonium compounds it is advantageous if an alkanolamine, for example monoethanolamine, is added to the aqueous solution. The fluid reaction medium can then be removed by evaporation, preferably by heating. When water is used as the reaction medium, the water can be removed at 100° to 150° C., in particular at ca. 120° C. Then the catalyst system is preferably calcined, for example at temperatures between 200° and 400° C., for a period which can exceed ca. 1 to 2 hours.

The embodiment using a solid support is particularly preferred for the catalyst system according to the invention. The preferred supports are based on oxygen compounds of aluminum, or mixtures of various types of such oxygen compounds. A carrier system based on silicon dioxide and "activated silica" (compare Unger; Angewandte Chemie. 84, 331 (1972)) is especially preferred, especially a support comprising diatomaceous earth and submicroscopic pyrogenic silica (e.g., Aerosil ®, manufactured by Degussa, Inc.). The preferred mixture ratio of silicon dioxide (e.g. diatomaceous earth) and activated silica (e.g. Aerosil ®) is 14:2 to 9:2, more preferably 5:1. The ratio of catalyst to support can range within certain limits. Generally the catalyst comprises 5 to 80% by weight, preferably 20 to 70% b.w., based on the total weight (catalyst plus carrier).

The catalyst can then be prepared for use in a catalyst system by appropriate procedures such as granulating, pelletizing, tableting, and the like. Following granulation, pelletization or tableting, a tempering step can be repeated, e.g. at 300° to 500° C. for ca. 1 hour to ca. 24 hours.

The catalytically active system can be used as is, or, preferably, mixed with an inert material, such as quartz or zirconium dioxide. This latter preparation has economic and technological advantages; for example it is possible to improve the temperature profile and to stabilize the reactor conditions, etc.

The catalyst system according to the present invention can be used within a relatively broad temperature range in the oxidative dehydrogenation of isobutyric acid without noticeably reduced effectiveness or inactivation.

It is preferable to carry out the process between 300° to 450° C., particularly between 340° and 370° C. In that range the contact times are generally between 0.1 and 5 sec. If in the course of the catalytic procedure temperatures occur that are above the optimal temperature range, this does not, as a rule, cause irreversible inactivation of the catalyst system. The catalyst systems according to the invention are characterized by excellent volume-time yields combined with high selectivity.

The oxidative dehydrogenation procedure according to the present invention makes use of oxygen as the oxidation medium, for example atmospheric oxygen. The reaction is advantageously performed as a gas phase reaction, operating with isobutyric acid and oxygen in the gas phase, preferably with a gas mixture of isobutyric acid, water, oxygen and nitrogen.

The ratio of the components, in the given sequence, varies advantageously within the following limits: (1–2.5):(0–3):(1–2):(4–10) mole. Particularly preferred in the ratio 1:2:1.7:20 mole. The presence of water typically has a favorable effect on the reaction.

The method according to the invention can be carried out in conventional reactors, for example, under pressure. The pressures used are 0.5 to 5 bar, preferably 0.8 to 20 bar. Increasing the amount of oxygen during the reaction can cause a significant increase in temperature, which does not as a rule, inactivate the catalyst system because of its unexpectedly great stability. In the process of the invention the catalysts can be used in a fixed bed or in a fluidized bed.

Having generally described the invention, a more complete understanding can be obtained by reference to certain specific examples, which are provided herein for purposes of illustration only, and are not intended to be limiting unless otherwise specified. Percentages, unless otherwise specified, are by weight.

The indicated conversions or selectivities are defined as follows:

Conversion of isobutyric acid (%) =

$$\frac{\text{moles of isobutyric acid reacted}}{\text{moles of isobutyric acid used}} \cdot 100$$

Selectivity of the methacrylic acid formation (%) =

$$\frac{\text{moles of methacrylic acid formed}}{\text{moles of isobutyric acid reacted}} \cdot 100$$

(A) Production of the catalysts

1. To a solution of 106 g of $(NH_4)_6Mo_7O_{24}\cdot 4H_2O$ in 300 ml of a 10% ammonia solution are added 11.52 g of 85% orthophosphoric acid, dissolved in 100 ml of water and the total resulting mixture is stirred into a solution of 19.4 g of cesium nitrate in 200 ml of water. Then, 8.8 g of $NH_4VO_3$, dissolved in 140 ml of 10% aqueous monoethanolamine, are added. The resulting solution is stirred and evaporated after 40.84 g of purified and ignited diatomacious earth and 8.18 g of Aerosil® submicroscopic pyrogenic silica are added to serve as catalyst supports. The solid catalyst mass is dried for 7 hours and then calcined for 3 hours at 300° C. The resulting 70% $Cs_2Mo_{12}V_{1.5}P_2O_{45.8}$ catalyst on diatomaceous earth/Aerosil® 200 is a very hard mass from which catalyst granules having a grain size of ca. 3 mm are prepared for filling the reactor.

2. The procedure of (Par.A) 1 is followed to produce the catalyst $Cs_{1.5}Mo_{12}V_{1.5}P_2O_{45.5}$ with the amount of added cesium nitrate reduced to 14.62 g.

3. The procedure (Par.A) 1 is followed to produce the catalysts tested and listed in the table. In the place of the Cs-salt of (A) 1, the equivalent amount of the corresponding metal shown in the table is added in the form of a salt.

(B) Process for oxidative dehydrogenation of isobutyric acid

EXAMPLE 1

A gaseous mixture of isobutyric acid, water, oxygen and nitrogen in a molar ratio of 1:2:1.8:20 was passed over 14.9 ml of a contact catalyst produced according to (A) 1 in a steel reactor at 350° C. and with a contact time of 0.9 sec. After an activation time of 20 hours, methacrylic acid yields of 69% of theoretical were attained with isobutyric acid conversions of 100%.

EXAMPLE 2

In a glass reactor containing 20 ml of the catalyst produced according to (A) 1, oxidation of isobutyric acid was carried out at 360° C., with a contact time of 0.6 sec. using a gaseous mixture of isobutyric acid, water, oxygen and nitrogen in a molar ratio of 1:2:1.8:20. Over a period of 150 hours the isobutyric acid conversion reached 99.5% and the methacrylic acid selectivity reached 70%.

EXAMPLE 3

A vapor mixture containing isobutyric acid, methacrylic acid, water and atmospheric oxygen in a molar ratio of 0.3:0.49:0.98:1.1 was passed over the catalyst produced according to (A) 1 in a glass reactor as the second step in a two-step reaction at 350° C. with a contact time of 0.4 sec. After this procedure, a total isobutyric acid conversion of 98% and a methacrylic acid selectivity of 71.3 over both steps was measured.

EXAMPLE 4

When the isobutyric acid dehydrogenation according to Example 1 was performed with the catalyst produced according to (A) 2, practically the same isobutyric acid conversions and methacrylic acid yields were obtained as with the catalyst according to (A) 1.

EXAMPLES 5-17

The results of additional experiments using catalysts of the general formula:

$$M_aMo_bV_cP_dO_e$$

in the oxidative dehydrogenation of isobutyric acid to methacrylic acid are summarized in Table 1 below.

In these tests mixtures of isobutyric acid, water, and atmospheric oxygen in a molar ratio of 1:2:1.7 were passed over the catalysts in a temperature range of 340° to 370° C. with contact times of 0.3 to 0.4 seconds.

TABLE I

| Example No. | Catalyst temperature °C. | Catalyst | Conversion of isobutyric acid % | Selectivity for Methacrylic Acid % |
|---|---|---|---|---|
| 5 | 350 | $Na_2Mo_{12}V_{1.5}P_2O_{48.8}$ | 70 | 60 |
| 6 | 370 | $K_2Mo_{12}V_{1.5}P_2O_{45.8}$ | 95 | 64 |
| 7 | 360 | $Rb_2Mo_{12}V_{1.5}P_2O_{45.8}$ | 98 | 66 |
| 8 | 340 | $BeMo_{12}V_{1.5}P_2O_{45.8}$ | 97.8 | 57 |
| 9 | 340 | $MgMo_{12}V_{1.5}P_2O_{45.8}$ | 86.4 | 63.4 |
| 10 | 370 | $CaMo_{12}V_{1.5}P_2O_{45.8}$ | 98.2 | 65.5 |
| 11 | 340 | $BaMo_{12}V_{1.5}P_2O_{45.8}$ | 80 | 57 |
| 12 | 370 | $Ag_2Mo_{12}V_{1.5}P_2O_{45.8}$ | 96 | 60 |
| 13 | 350 | $ZnMo_{12}V_{1.5}P_2O_{46.8}$ | 96.5 | 57 |
| 14 | 360 | $Al_{0.67}Mo_{12}V_{1.5}P_2O_{45.3}$ | 99.2 | 65.6 |
| 15 | 360 | $PbMo_{12}V_{1.5}P_2O_{45.8}$ | 70 | 60 |
| 16 | 340 | $SnMo_{12}V_{1.5}P_2O_{45.8}$ | 80 | 45 |
| 17 | 350 | $TiMo_{12}V_{1.5}P_2O_{45.8}$ | 77.8 | 64.8 |

EXAMPLES 18-24

By a method analogous to the procedure of (A) 3, four catalysts, A to D having the following composition were produced:

(A) Mn $Mo_{12}V_{1.5}P_2O_{45.8}$
(B) $Fe_{0.67}Mo_{12}V_{1.5}P_2O_{45.8}$
(C) Co $Mo_{12}V_{1.5}P_2O_{45.8}$
(D) Ni $Mo_{12}V_{1.5}P_2O_{45.8}$

Mixtures of isobutyric acid, water and atmospheric oxygen in a molar ratio of 1:2:1.7 were passed over the catalysts A to D in a temperature range of 320°–350° C. with a contact time of 0.3 sec. The resultant values for the isobutyric acid conversion and the methacrylic acid selectivity are summarized in Table II below.

TABLE II

| Example No. | Catalyst | Catalyst Temperature °C. | Conversion of Isobutyric acid (%) | Methacrylic acid selectivity (%) |
|---|---|---|---|---|
| 18 | A | 330 | 84.8 | 64.9 |
| 19 | A | 340 | 93.0 | 62.3 |
| 20 | B | 330 | 81.8 | 66.1 |
| 21 | B | 350 | 95.9 | 62.3 |
| 22 | C | 340 | 91.1 | 65.5 |
| 23 | C | 350 | 96.1 | 64.5 |
| 24 | D | 350 | 93.6 | 58.4 |

EXAMPLE 25

A gaseous mixture of isobutyric acid, water, oxygen and nitrogen in a molar ratio of 1:2:1.5:20 was passed over 13 ml of a catalyst of composition C of Examples 18–24 precipitated on diatomaceous earth, with a contact time of 0.5 sec. at 360° C. At a conversion of 99.8% of the isobutyric acid used, methacrylic acid was produced with a selectivity of 74.1%.

Having now fully described the invention, it will be apparent to one of ordinary skill in the art that many changes and modification can be made thereto without departing from the spirit or scope of the invention as set forth herein.

What is claimed as new and desired to be secured by Letters Patent of the United States is:

1. A process for producing methacrylic acid or an ester thereof comprising contacting in gaseous phase in presence of oxygen isobutyric acid or the corresponding ester thereof with a metal oxide catalyst substantially free of sulfate and consisting essentially of oxides of molybdenum, vanadium, phosphorus, and a metal selected from the group consisting of alkali metals, alkaline earth metals, zinc, silver, aluminum, titanium, lead, manganese, iron, cobalt, nickel, and tin.

2. The process of claim 1, wherein said metal oxide catalyst has the formula:

$$M_aMo_bV_cP_dO_e$$

wherein M is a metal selected from the group consisting of K, Rb, Cs, Be, Mg, Ba, Zn, Ca, Ag, Al, Ti, Pb, Mn, Fe, Co, Ni, and Sn;

a is a number from 0.4 to 2.5;
b is a number about equal to 12;
c is a number from 1 to 2;
d is a number from 0.5 to 3; and
e is a number chosen to satisfy the valences and amounts of the other elements present in the catalyst.

3. The process of claim 1 or 2, wherein said metal oxide catalyst has the formula:

$$A_{1.5-2}Mo_{12}V_{1.5}P_2O_{45-46}$$

wherein A is an alkali metal selected from the group consisting of potassium, rubidium and cesium.

4. The process of claim 1 or 2, wherein the metal oxide catalyst is supported on a solid support comprising silicon dioxide and activated silica.

5. The process of claim 4, wherein said silicon dioxide is diatomaceous earth and said activated silica is submicroscopic pyrogenic silica.

6. The process of claim 4, wherein the ratio of silicon dioxide/activated silica in said support is 14:2 to 9:2.

7. The process of claim 6, wherein said ratio is 5:1.

8. The process of claim 1 or 2, wherein said metal oxide catalyst comprises 5 to 80% by weight of the total weight of support plus metal oxide catalyst.

9. The process of claim 8 wherein said metal oxide catalyst comprises 20 to 70% by weight of the total weight of support plus metal oxide catalyst.

10. The process of claim 1 or 2, wherein said catalyst is calcined at temperatures between 200° and 400° C. before being used in the process.

11. The process of claims 1 or 2, wherein said isobutyric acid or ester thereof is in the gas phase.

12. The process of claim 11, wherein said isobutyric acid or ester thereof is present in a mixture together with water, oxygen and nitrogen.

13. The process of claim 12, wherein the molar ratio of isobutyric acid or ester thereof to water to oxygen to nitrogen is (1–2.5):(0–3):(1–2):(4–10).

14. The process of claim 13, wherein said molar ratio is 1:2:1.7:20.

15. The process of claim 1 or 2, wherein said oxidative dehydrogenation is performed in a temperature range of 300° to 450° C.

16. The process of claim 15, wherein said temperature range is 340° to 450° C.

17. The process of claim 15, wherein said temperature range is 340° to 370° C.

18. The process of claim 12, wherein said gaseous mixture is introduced at a space velocity of about 100 to 15,000 liters of gas per liter of catalyst per hour.

19. The process of claim 11, wherein the pressure of said gas is from 0.5 to 5 bar.

20. The process of claim 12, wherein the pressure of said gas mixture is 0.5 to 5 bar.

21. The process of claim 1 or 2, wherein said metal oxide catalyst contains a metal selected from the group consisting of magnesium, calcium and aluminum.

* * * * *